United States Patent
Kawakami et al.

(10) Patent No.: US 10,137,098 B2
(45) Date of Patent: Nov. 27, 2018

(54) TRANSDERMAL PREPARATION

(71) Applicant: TEIKOKU SEIYAKU CO., LTD., Kagawa (JP)

(72) Inventors: Satoshi Kawakami, Kagawa (JP); Taiki Shibata, Kagawa (JP); Manabu Sogabe, Kagawa (JP)

(73) Assignee: TEIKOKU SEIYAKU CO., LTD., Kagawa (JP)

( * ) Notice: Subject to any disclaimer, the term of this patent is extended or adjusted under 35 U.S.C. 154(b) by 0 days.

(21) Appl. No.: 15/311,670

(22) PCT Filed: May 20, 2015

(86) PCT No.: PCT/JP2015/064526
§ 371 (c)(1),
(2) Date: Nov. 16, 2016

(87) PCT Pub. No.: WO2015/182459
PCT Pub. Date: Dec. 3, 2015

(65) Prior Publication Data
US 2017/0079940 A1  Mar. 23, 2017

(30) Foreign Application Priority Data
May 28, 2014 (JP) .............................. 2014-110446

(51) Int. Cl.
| *A61K 31/18* | (2006.01) |
| *A61K 47/10* | (2017.01) |
| *A61K 9/70* | (2006.01) |
| *A61K 47/34* | (2017.01) |
| *A61K 31/404* | (2006.01) |
| *A61K 47/32* | (2006.01) |

(52) U.S. Cl.
CPC ............... *A61K 31/18* (2013.01); *A61K 9/70* (2013.01); *A61K 9/7061* (2013.01); *A61K 31/404* (2013.01); *A61K 47/10* (2013.01); *A61K 47/32* (2013.01); *A61K 47/34* (2013.01)

(58) Field of Classification Search
CPC .................................................... A61K 31/18
USPC ....................................................... 514/415
See application file for complete search history.

(56) References Cited

U.S. PATENT DOCUMENTS

| 6,231,885 B1 | 5/2001 | Carrara | |
| 2009/0155343 A1* | 6/2009 | Kawahara | A61K 9/7053 424/449 |
| 2013/0211353 A1* | 8/2013 | Toshimitsu | A61K 31/4045 604/307 |

FOREIGN PATENT DOCUMENTS

| EP | 0 416 804 | 3/1991 |
| JP | 11152224 | 6/1999 |
| WO | 2007/119656 | 10/2007 |
| WO | 2012/057212 | 5/2012 |
| WO | 2012/105625 | 8/2012 |

OTHER PUBLICATIONS

Definition of "Tamsulosin" in Wikipedia downloaded Jan. 23, 2018.*
Definition of "Silodosin" in Wikipedia downloaded Jan. 23, 2018.*
International Search Report dated Jun. 23, 2015 in International (PCT) Application No. PCT/JP2015/064526.
Yokoyama et al., "Cross-over study of tamsulosin hydrochloride and silodosin for benign prostatic hypertrophy", The Nishinihon Journal of urology, vol. 72, special extra issue, Oct. 20, 2010, p. 123, with English translation.
European Search Report dated Sep. 29, 2017 in European Application No. 15800275.8.

* cited by examiner

Primary Examiner — Yong L Chu
(74) Attorney, Agent, or Firm — Wenderoth, Lind & Ponack, L.L.P.

(57) ABSTRACT

Provided is a novel transdermal absorption preparation containing silodosin or tamsulosin, or salt thereof as an active ingredient, wherein the transdermal absorption preparation is capable of keeping a dissolved state for a long time, as well as has a high permeability to a skin, and can effectively and sustainably exert the transdermal absorbability. A transdermal absorption preparation containing the transdermal absorption preparation comprises an acrylic pressure-sensitive adhesive that comprises a copolymer of at least one (meth)acrylic acid monomer and at least one vinyl monomer and that contains a carboxyl group, and at least one transdermal absorption promoting agent selected from the group consisting of oleyl alcohol, lauryl alcohol, and lauromacrogol.

7 Claims, No Drawings

TRANSDERMAL PREPARATION

TECHNICAL FIELD

The present invention relates to a transdermal absorption preparation containing an α1-blocker such as silodosin or tamsulosin as an active ingredient.

BACKGROUND ART

An α1-adrenoceptor blocker (α1-blocker) is currently most often used as a drug for improving dysuria caused by benign prostatic hypertrophy, and as examples thereof, silodosin, tamsulosin hydrochloride, urapidil, naftopidil, terazosin hydrochloride hydrate, and the like can be given.

Currently, α1-blockers are mainly administered orally in clinical practice. However, in the case of oral administration, since a drug undergoes its metabolism (first-pass effect) in a digestive tract and liver, the number of administrations and the amount of dose may increase, and hence there are problems such as occurrence of side effects such as liver failure. In order to solve such problems, transdermal absorption preparations of the α1-blocker have been proposed. By making it into a transdermal absorption preparation, the drug efficacy is exerted sustainably for a long time, whereby the number of administrations and the amount of dose of the drug can be decreased, and advantages such as improvement of compliance due to a simplified administration, easiness of discontinuing the administration, or the like can be obtained.

Generally, a transdermal absorption preparation such as a skin patch is composed of a pressure-sensitive adhesive layer containing a drug, a backing for supporting the pressure-sensitive adhesive layer, and a release liner that covers the pressure-sensitive adhesive layer. The release liner is removed before using and applied to a prescribed place. In order to efficiently and sustainably exert the transdermal absorption action of the drug, it is necessary that the drug having a concentration as high as possible be dissolved in the pressure-sensitive adhesive (the drug solubility), and that said drug be sustainably released from the pressure-sensitive adhesive and be shifted to the skin (the release characteristics of a drug or the skin permeability of a drug). If the drug solubility is insufficient, crystals of the drug are formed in the pressure-sensitive adhesive, leading to a reduction in drug release, and hence a sufficient transdermal absorbability cannot be obtained. Furthermore, when it is impossible to achieve the intended amount of transdermal absorption by merely dissolving the drug in the pressure-sensitive adhesive, a prescribed transdermal absorption promoting agent must be added to increase the amount of transdermal absorption.

Several transdermal absorption preparations containing an α1-blocker have heretofore been proposed.

For example, Patent Document 1 discloses a percutaneous absorption preparation containing silodosin and a percutaneous absorption promoting agent such as oleyl alcohol, wherein the percutaneous absorption preparation further contains a fatty acid ester and/or a fatty acid amide that further improve the function of the percutaneous absorption promoting agent. In Patent Document 1, from the viewpoint that silodosin and the like have low skin permeability, and in order to use them in a skin-absorption type preparation wherein a drug is absorbed through the skin, their skin permeability must be increased, the above-mentioned fatty acid ester and/or fatty acid amide are used as essential components.

Furthermore, Patent Document 2 discloses a transdermal patch containing tamsulosin as an α1-blocker and an acrylic adhesive. Tamsulosin is slightly-soluble in various solvents and has a low solubility thereof relative to an adhesive, and hence there is a problem that when tamsulosin is used as it is, it exists in a crystalline state in the adhesive layer. For this reason, in Patent Document 2, a specific type of base resin having high performance of dissolving tamsulosin, that is, an acrylic adhesive based on a copolymer of a monomer having a pyrrolidone ring and a (meth)acrylic acid alkyl ester with a carbon atom number of the alkyl group of 4 to 12 is adopted as a base resin itself in the adhesive, and the solubility of tamsulosin in the adhesive layer is enhanced. In addition, it is described that tamsulosin can be dissolved in a higher concentration in the adhesive layer by using polyoxyethylene lauryl ether (lauromacrogol) preferably.

PRIOR ART DOCUMENT

Patent Document

Patent Document 1: WO 2012/057212 pamphlet
Patient Document 2: WO 2007/119656 pamphlet

DISCLOSURE OF THE INVENTION

Problems to be Solved by the Invention

As described above, various techniques to improve the solubility and the skin permeability of a drug have heretofore been proposed for transdermal absorption preparations containing an α1-blocker, but further improvement is demanded.

For example, the above-mentioned Patent Document 1 describes that the content of silodosin in the percutaneous absorption preparation is preferably 1 to 10 mass %, and more preferably 3 to 7 mass %, and only discloses the preparation containing silodosin of at most 5 mass % in the examples. However, it is assumed that in order to sustainably exert transdermal absorbency of silodosin for a long period, for example, more than 15 hours, it is necessary that the preparation contain silodosin in a high concentration of at least more than 5 mass %, and the preparation of Patent Document 1 cannot respond to such a demand. In addition, it is necessary that the preparation have sufficient adhesion (cohesiveness) when applied to a skin as a percutaneous absorption preparation, and further improvement is needed from these viewpoints.

Furthermore, the acrylic adhesive used in the tamsulosin-containing transdermal patch of the above-mentioned Patent Document 2 has an insufficient solubility of tamsulosin and may not keep the solubility for a long period.

The present invention has been made in view of the above situation, and an object of the present invention is to provide a novel transdermal absorption preparation containing silodosin or tamsulosin, or salt thereof as an active ingredient, wherein the transdermal absorption preparation is capable of keeping a dissolved state for a long time, as well as has a high permeability to a skin, and can effectively and sustainably exert the transdermal absorbability.

Means for Solving the Problems

A transdermal absorption preparation of the present invention, which can solve the above problems, containing silodosin or a salt thereof, or tamsulosin or a salt thereof as an active ingredient, wherein the transdermal absorption preparation comprises an acrylic pressure-sensitive adhesive that comprises a copolymer of at least one (meth)acrylic acid monomer and at least one vinyl monomer and that contains a carboxyl group, and at least one transdermal absorption promoting agent selected from the group consisting of oleyl alcohol, lauryl alcohol, and lauromacrogol.

In a preferred embodiment of the present invention, the transdermal absorption preparation, wherein a content of the silodosin or a salt thereof in the transdermal absorption preparation is 10 to 50 mass % in terms of a free form of silodosin.

In a preferred embodiment of the present invention, the transdermal absorption preparation, wherein a content of the tamsulosin or a salt thereof in the transdermal absorption preparation is 0.5 to 10 mass % in terms of a free form of tamsulosin.

In a preferred embodiment of the present invention, the transdermal absorption preparation, wherein the transdermal absorption promoting agent is lauromacrogol.

In a preferred embodiment of the present invention, the transdermal absorption preparation, wherein the (meth) acrylic acid monomer comprises at least one selected from the group consisting of acrylic acid, methacrylic acid, and derivatives thereof.

In a preferred embodiment of the present invention, the transdermal absorption preparation, wherein the vinyl monomer comprises at least one selected from the group consisting of vinyl acetate, N-vinyl-2-pyrrolidone, acrylamide, dimethylacrylamide, diethylacrylamide, methacrylamide, N-methylolacrylamide, glycidyl acrylate, and glycidyl methacrylate.

Effects of the Invention

The transdermal absorption preparation of the present invention is formed by combining a specific pressure-sensitive adhesive and a specific transdermal absorption promoting agent, and therefore silodosin or tamsulosin, or salt thereof that is an active ingredient can be kept in a dissolved state for a long time, for example, 24 hours or longer, and excellent transdermal absorbability can be achieved.

According to the present invention, it is possible to provide a transdermal absorption preparation containing silodosin in a higher concentration than, for example, that in the preparation of Patent Document 1.

Furthermore, according to the present invention, it is possible to provide a transdermal absorption preparation containing tamsulosin capable of keeping a dissolved state for a long time, for example, as compared with the preparation of Patent Document 2.

With the transdermal absorption preparation of the present invention, it is possible to rapidly increase the blood level of silodosin or tamsulosin that is an active ingredient in the blood after administration and maintain an effective blood level over a long period of time. Thus, according to the present invention, silodosin or tamsulosin can be efficiently absorbed into the blood through the skin, thereby having advantages that side effects on the digestive system that are found in oral administration and side effects on the nervous system that may be caused by a sudden increase in blood level can be avoided. Therefore, the transdermal absorption preparation of the present invention is extremely effective in the treatment of urinary frequency, urinary incontinence, dysuria, and the like.

MODE FOR CARRYING OUT THE INVENTION

The inventors of the present invention made studies to solve the above problems in a transdermal absorption preparation containing silodosin or a salt thereof, or tamsulosin or a salt thereof. As a result, the inventors have found that the predetermined object is achieved by using the following (1) as a pressure-sensitive adhesive and the following (2) as a transdermal absorption promoting agent in combination, and thus the present invention has been completed:

(1) an acrylic pressure-sensitive adhesive that includes a copolymer of at least one (meth)acrylic acid monomer and at least one vinyl monomer and that contains a carboxyl group (hereinafter, may be referred to as "a pressure-sensitive adhesive of a carboxyl group-containing acrylic acid-vinyl copolymer" or simply "a pressure-sensitive adhesive"), and (2) at least one transdermal absorption promoting agent selected from the group consisting of oleyl alcohol, lauryl alcohol, and lauromacrogol.

As described above, the present invention has the most important feature in that a specific pressure-sensitive adhesive and a specific transdermal absorption promoting agent are used in combination. The pressure-sensitive adhesive and the transdermal absorption promoting agent used in the present invention are known and have been used in the field of transdermal absorption preparations. However, there has been no transdermal absorption preparation containing an α1-blocker such as silodosin or tamsulosin using the pressure-sensitive adhesive and the transdermal absorption promoting agent in combination, and the fact that the solubility of silodosin or tamsulosin and the amount of skin permeation of the drug are remarkably enhanced by this combination has been firstly found by the present inventors.

In particular, as for the specific pressure-sensitive adhesive used in the present invention, it is important in the present invention to use a (meth)acrylic copolymer that is a copolymer of a (meth)acrylic acid monomer and a vinyl monomer and that contains a carboxyl group is used. Examples given later demonstrate that if a "copolymer of a (meth)acrylic acid monomer and a vinyl monomer" that contains a functional group other than a carboxyl group (COOH group), for example, a hydroxyl group (OH group), or contains no functional group is used, the desired effects cannot be obtained.

For example, in the percutaneous absorption preparation containing silodosin described in the above-mentioned Patent Document 1, examples of usable pressure-sensitive adhesives include acrylic type pressure-sensitive adhesive, rubber type pressure-sensitive adhesive, silicone type pressure-sensitive adhesive, etc. However, in the present invention, the examples given later demonstrate that the desired effects cannot be obtained even when the above rubber type pressure-sensitive adhesive or silicone type pressure-sensitive adhesive other than the acrylic type pressure-sensitive adhesive is used.

Furthermore, the above-mentioned Patent Document 1 has only an understanding that "the acrylic pressure-sensitive adhesive is not particularly limited as long as it is a copolymer comprising at least one (meth)acrylic acid derivative represented by 2-ethylhexyl acrylate, methyl acrylate, butyl acrylate, hydroxyethyl acrylate, 2-ethylhexyl methacrylate, etc." as usable acrylic pressure-sensitive adhesives, and does not disclose or suggest that an acrylic pressure-sensitive adhesive containing a carboxyl group is useful, like the present invention.

Furthermore, the above-mentioned Patent Document 1 also exemplifies a "copolymer of a (meth)acrylic acid monomer and a vinyl monomer", but describes that "in particular, acrylic pressure-sensitive adhesives having a hydroxyl group can be preferably used from the viewpoint of drug release characteristics", and the experiment using the same was only conducted in the examples. Therefore, it is clear that the above-mentioned Patent Document 1 does not intend to use an acrylic pressure-sensitive adhesive containing a carboxyl group, like the present invention. In addition, based on Patent Document 1, it is absolutely impossible to arrive at usefulness achieved by using the "pressure-sensitive adhesive of a carboxyl group-containing acrylic acid-vinyl copolymer", like the present invention.

Moreover, in the percutaneous absorption preparation containing silodosin described in the above-mentioned Patent Document 1, in order to improve the transdermal absorbability of silodosin, a fatty acid ester and/or fatty acid amide that further improve the function of the percutaneous absorption promoting agents are used as essential components in addition to percutaneous absorption promoting agents such as triacetin, isopropyl myristate, oleyl alcohol, and the like. The present invention also differs in composition from the above-mentioned Patent Document 1 in that the above fatty acid ester and/or fatty acid amide are not used.

It should be noted that although oleyl alcohol, which is a transdermal absorption promoting agent used in the present invention, is exemplified also in Patent Document 1, Patent Document 1 significantly differs in composition from the present invention in that experiments using triacetin were conducted in the most of the examples of Patent Document 1, and the usefulness of fatty acid ester and/or fatty acid amide is considered based on these experiments; Patent Document 1 does not disclose examples using a "pressure-sensitive adhesive of a carboxyl group-containing acrylic acid-vinyl copolymer" at all as described above; and therefore Patent Document 1 does not disclose the combination of the specific pressure-sensitive adhesive and the specific transdermal absorption promoting agent defined in the present invention.

Furthermore, as for the tamsulosin-containing transdermal patch described in the above-mentioned Patent Document 2, it is described that a polyoxyethylene lauryl ether (lauromacrogol) can be used as a transdermal absorption promoting agent, and a pressure-sensitive adhesive based on a copolymer of a monomer having a pyrrolidone ring and a (meth)acrylic acid alkyl ester can be preferably used. However, Patent Document 2 does not describe the use of an acrylic pressure-sensitive adhesive that is a copolymer of an acrylic monomer and a vinyl monomer and that contains a carboxyl group, like the present invention, and considering the composition of the examples, it is impossible to arrive at the acrylic pressure-sensitive adhesive of the present invention.

Hereinafter, the components constituting the preparation of the present invention will be described in detail.

1. Active Ingredient

In the present invention, silodosin or tamsulosin is used as an α1-blocker. In the present invention, these drugs may be used in a free form (free-type) and a salt thereof can be used.

The above salt is not limited as long as it is a pharmaceutically acceptable salt. As examples of such salt, acid addition salt with a medically acceptable inorganic or organic acid such as hydrochloride, acetic acid salt, tartrate, oxalate, citrate, or the like can be given.

When the active ingredient is silodosin or a salt thereof, the content of silodosin in the transdermal absorption preparation, i.e. the content of silodosin when the total content of silodosin or a salt thereof, an acrylic pressure-sensitive adhesive, and a transdermal absorption promoting agent is taken as 100 mass % (in the case of a salt of silodosin, a value converted to a free form) is not particularly limited as long as preparations can be formulated, but the content is preferably 10 mass % or more and 50 mass % or less in order to allow the desired effects to be effectively exhibit. If the content of silodosin is less than 10 mass %, sustained transdermal absorption effects cannot be obtained. The content is preferably 10 mass % or more, and more preferably 15 mass % or more. On the other hand, if the content of silodosin is more than 50 mass %, crystals may be deposited due to insufficient solubility of silodosin, and therefore, the content of silodosin is preferably 50 mass % or less. It is more preferably 40 mass % or less, and further preferably 30 mass % or less.

When the active ingredient is tamsulosin or a salt thereof, the content of tamsulosin in the transdermal absorption preparation (in the case of a tamsulosin salt, a value converted to a free form) is not particularly limited as long as preparations can be formulated, but the content is preferably 0.5 mass % or more and 10 mass % or less in order to allow the desired effects to be effectively exhibit. If the content of tamsulosin is less than 0.5 mass %, a sufficient transdermal absorption effect cannot be obtained. The content is preferably 0.5 mass % or more, more preferably 1 mass % or more, and further preferably 2 mass % or more. On the other hand, if the content of tamsulosin is more than 10 mass %, crystals may be deposited due to insufficient solubility of tamsulosin, and therefore, the content of tamsulosin is preferably 10 mass % or less. It is more preferably 8 mass % or less, and further preferably 5 mass % or less.

2. Pressure-Sensitive Adhesive

The transdermal absorption preparation of the present invention includes, as an adhesive, an acrylic pressure-sensitive adhesive that is a copolymer of at least one (meth)acrylic acid monomer and at least one vinyl monomer and that contains a carboxyl group (a pressure-sensitive adhesive of a carboxyl group-containing acrylic acid-vinyl copolymer).

As examples of the (meth)acrylic acid monomer used in the present invention, acrylic acid, methacrylic acid, and derivatives thereof can be given. They can be used singly or in combination of two or more. As examples of the above derivatives, a (meth)acrylic acid ester can be given. Specifically, examples of the acrylic acid ester include n-butyl acrylate, n-hexyl acrylate, n-octyl acrylate, 2-ethylhexyl acrylate, isooctyl acrylate, isononyl acrylate, n-decyl acrylate, isodecyl acrylate, and the like. Examples of the methacrylic acid ester include n-decyl methacrylate, dodecyl methacrylate, 2-ethylhexyl methacrylate, isodecyl methacrylate, lauryl methacrylate, and the like. These (meth)acrylic acid esters can be used singly or in combination of two or more. Taking the solubility and the time-course stability of drug into consideration, 2-ethylhexyl acrylate and 2-ethylhexyl methacrylate are preferable among the above (meth)acrylic acid esters.

As examples of the above-mentioned vinyl monomer used in the present invention, compounds having one or more vinyl groups in their molecule can be given. The compounds may have other functional groups within a range that does not impair the action of the invention. Examples of such vinyl monomers include vinyl ester monomers such as vinyl acetate; monomers having a pyrrolidone ring such as N-vinyl-2-pyrrolidone; amide monomers such as acrylamide, dimethylacrylamide, diethylacrylamide, methacrylamide, and N-methylolacrylamide; and monomers having an epoxy group such as glycidyl acrylate and glycidyl methacrylate. These vinyl monomers can be used singly or in combination of two or more. Taking the solubility and the time-course stability of drug into consideration, vinyl acetate is particularly preferable among the above vinyl monomers.

It is important that the copolymer of a (meth)acrylic acid monomer and a vinyl monomer used in the present invention contains a carboxyl group. For example, it is impossible to allow a carboxyl group to exist in the copolymer by a mere reaction of 2-ethylhexyl acrylate with N-vinyl-2-pyrrolidone as described in the Example 4 of the above-mentioned Patent Document 2. In the above example, it is necessary, for example, to further add a (meth)acrylic acid and conduct a reaction.

As the pressure-sensitive adhesive of a carboxyl group-containing acrylic acid-vinyl copolymer used in the present invention, commercially-available products can be used. Specifically, for example, acrylic pressure-sensitive adhesives such as Duro-Tak 87-2194, Duro-Tak 87-2196, Duro-Tak 87-2051, and Duro-Tak 87-2852 manufactured by Henkel can be given.

In contrast, both of Duro-Tak 87-2516 and Duro-Tak 87-2287 manufactured by Henkel, which are acrylic pressure-sensitive adhesives having no carboxyl group and having a hydroxyl group, are not used in the present invention because the desired effects cannot be obtained (see Examples given later). Furthermore, Duro-Tak 87-4098 manufactured by Henkel, which is an acrylic pressure-sensitive adhesive having no functional groups such as carboxyl groups, is not used in the present invention because the desired effects cannot be obtained (see Examples given later).

The content of the above pressure-sensitive adhesive in the transdermal absorption preparation of the present invention is not particularly limited as long as it is within a range which allows the desired effects to be effectively exhibited, but it is preferred to be roughly within the range of 30 to 98.5 mass %. When the content of the pressure-sensitive adhesive is less than 30 mass %, there is a problem that the pressure-sensitive adhesive may be left on a skin due to insufficient cohesive force of the pressure-sensitive adhesive layer. The content is preferably 30 mass % or more, more preferably 40 mass % or more, and further preferably 50 mass % or more. On the other hand, when the content of the above pressure-sensitive adhesive is more than 98.5 mass %, the concentration of the drug becomes low, and hence a sufficient transdermal absorbability cannot be obtained. The content is preferably 98.5 mass % or less, more preferably 95 mass % or less, and further preferably 90 mass % or less.

3. Transdermal Absorption Promoting Agent

In the present invention, at least one selected from the group consisting of oleyl alcohol, lauryl alcohol, and lauromacrogol are contained as a transdermal absorption promoting agent. These may be contained singly or in an arbitrary combination of two or more. Taking the solubility and the transdermal absorbability of drug into consideration, it is preferred to contain lauromacrogol.

The content of the above transdermal absorption promoting agent in the transdermal absorption preparation of the present invention the case where a single agent is contained, the content of the single agent, and in the case where two or more agents are contained, the total content of these agents) is not particularly limited as long as it is within a range which allows the desired effects to be effectively exhibited, but it is preferred to be roughly within the range of 1 mass % or more and 30 mass % or less. When the content of the transdermal absorption promoting agent is less than 1 mass %, excellent transdermal absorbability cannot be obtained. The content is preferably 1 mass % or more, more preferably 5 mass % or more, and further preferably 10 mass % or more. On the other hand, when the content of the transdermal absorption promoting agent exceeds 30 mass %, skin irritation such as redness or swelling may occur. The content is preferably 30 mass % or less, more preferably 25 mass % or less, and further preferably 20 mass % or less.

According to the transdermal absorption preparation of the present invention, a sufficient transdermal absorbability can be obtained even if a component (a fatty acid ester or a fatty acid amide) that further improves the function of the percutaneous absorption promoting agent as described in the above-mentioned Patent Document 1 is not blended.

4. Others

The preparation of the present invention is composed of the above-mentioned active ingredient, transdermal absorption promoting agent, and pressure-sensitive adhesive. In addition to the above-mentioned components, the preparation of the present invention may contain additives that are usually used in transdermal absorption preparations within a range that does not impair the action of the invention, if necessary.

For example, for the sake of the adhesion and the stability of a pressure-sensitive adhesive base, the preparation of the present invention may contain, for example, an appropriate amount of a softening agent such as polyisobutylene, polybutene, liquid paraffin or the like; a water-soluble polymer such as polyvinylpyrrolidine, polyvinyl alcohol or the like; a cellulose derivative such as ethylcellulose, hydroxypropylcellulose, hydroxypropyl methylcellulose or the like; an inorganic filler such as a silicon compound such as anhydrous silicic acid or light anhydrous silicic acid, silica or the like; and an antioxidant such as dibutylhydroxytoluene or the like. If further need arises, an appropriate amount of a preservative, an algefacient, a fungicide, a flavoring agent, a colorant, and the like may be contained.

Hereinbefore, the components constituting the preparation of the present invention are explained.

The transdermal absorption preparation of the present invention may be used as a laminated structure in which a pressure-sensitive adhesive composition containing the above-mentioned active ingredient, transdermal absorption promoting agent, and pressure-sensitive adhesive (and other additives, if necessary) is laminated on a backing, and then covered with a release liner. The release liner is peeled off before using, and the pressure-sensitive adhesive composition side is applied to a skin.

The above-mentioned backing used in the present invention is not particularly limited, and a normally-used elastic or non-elastic backing for a patch can be given. Specifically, a film or sheet composed of a synthetic resin such as polyethylene terephthalate (hereinafter, may be referred to as PET), polyethylene, polypropylene, polybutadiene, an ethylene-vinyl acetate copolymer, polyvinyl chloride, polyester, nylon, polyurethane, or the like, or a laminate of these, a porous membrane, a foam, a woven fabric, a non-woven fabric, or a paper material can be used.

The above-mentioned release liner used in the present invention is not particularly limited as long as it is a normally-used liner for a patch. As examples thereof, PET, polypropylene, paper, or the like can be given, and PET is particularly preferable. The release liner may be siliconized if necessary in order to optimize the release force.

The transdermal absorption preparation of the present invention can be produced, for example, by the following method. First, the above-mentioned active ingredient, transdermal absorption promoting agent, and pressure-sensitive adhesive (and other additives, if necessary) are dissolved in an appropriate solvent to obtain a pressure-sensitive adhesive solution. As for the above solvent, an optimum one can be appropriately selected depending on the kinds of the constituent components, and for example, ethyl acetate, ethanol, methanol or the like can be used singly or in combination of two or more. Next, the pressure-sensitive adhesive solution thus obtained is spread on a release liner or a backing, the solvent is dried and removed, and then a backing or a release liner is applied thereto to obtain the transdermal absorption preparation of the present invention.

Here, the thickness of the pressure-sensitive adhesive layer (the layer containing the active ingredient, the transdermal absorption promoting agent, the pressure-sensitive adhesive, and if necessary, other additives) is preferably 30 μm or more and 200 μm or less. When the thickness is less than 30 μm, the sustainability of the drug release is reduced. It is preferably 30 μm or more, and more preferably 50 μm or more. Meanwhile, when the thickness is greater than 200 μm, the drug amount in the pressure-sensitive adhesive layer increases, leading to an increase in amount of remaining drug therein and an increase in cost. The thickness is preferably 200 μm or less, and further preferably 150 μm or less.

The present application claims the benefit of priority based on Japanese Patent Application No. 2014-110446 filed on May 28, 2014. The entire contents of the specification of Japanese Patent Application No. 2014-110446 filed on May 28, 2014 are incorporated herein by reference.

EXAMPLES

Hereinafter, the present invention will be illustrated in further detail with reference to Examples and Test Examples below. It should be noted, however, that the present invention is not limited to the following Examples. Unless otherwise specified in the following, "%" means "mass %".

(1) Experiments Using Silodosin as an Active Ingredient

Here, the following experiments were performed using silodosin (free form) as an active ingredient.

(1-1) Solubility Test of Silodosin (Basic Experiment)

First, in order to explore the usefulness of the pressure-sensitive adhesive used in the present invention, samples were produced based on the following Formulation Examples 1 to 10 composed of silodosin and various pressure-sensitive adhesives and containing no transdermal absorption promoting agent to examine the solubility of silodosin. The content of each component in each of the Formulation Examples is shown in Table 1. In Table 1, "—" means 0%.

Formulation Example 1

Silodosin was dissolved in a suitable amount of methanol to prepare a silodosin-containing solution. To the silodosin-containing solution thus obtained was added a carboxyl group-containing acrylic pressure-sensitive adhesive (Duro-Tak 87-2194), the resulting mixture was stirred and mixed to obtain a homogenous silodosin-containing pressure-sensitive adhesive solution. Next, this silodosin-containing pressure-sensitive adhesive solution was spread on a release liner (a PET film), and then the solvent was dried and removed to form a pressure-sensitive adhesive layer with the thickness of 50 μm. Then, a backing was applied thereto to obtain Formulation Example 1. The details of the prescription of Formulation Example 1 are shown in Table 1.

Formulation Example 2

Formulation Example 2 was obtained by the same production method as in Formulation Example 1 except that a hydroxyl group-containing acrylic pressure-sensitive adhesive (Duro-Tak 87-2516) was used as an acrylic pressure-sensitive adhesive (the thickness of the pressure-sensitive adhesive layer: 50 μm). The details of the prescription of Formulation Example 2 are shown in Table 1.

Formulation Example 3

Formulation Example 3 was obtained by the same production method as in Formulation Example 1 except that a hydroxyl group-containing acrylic pressure-sensitive adhesive (Duro-Tak 87-2287) was used as an acrylic pressure-sensitive adhesive (the thickness of the pressure-sensitive adhesive layer: 100 μm). The details of the prescription of Formulation Example 3 are shown in Table 1.

Formulation Example 4

Formulation Example 4 was obtained by the same production method as in Formulation Example 1 except that an acrylic pressure-sensitive adhesive having no functional groups (Duro-Tak 87-4098) was used as an acrylic pressure-sensitive adhesive (the thickness of the pressure-sensitive adhesive layer: 100 μm). The details of the prescription of Formulation Example 4 are shown in Table 1.

Formulation Examples 5 and 6

A suitable amount of ethyl acetate was added to silodosin to prepare a silodosin-containing solution. To the silodosin-containing solution thus obtained was added a silicone pressure-sensitive adhesive (BIO-PSA 7-4302 or BIO-PSA 7-4602), the resulting mixture was stirred and mixed to obtain a homogenous silodosin-containing pressure-sensitive adhesive solution. Next, this silodosin-containing pressure-sensitive adhesive solution was spread on a release liner (a PET film), and the solvent was dried and removed to form a pressure-sensitive adhesive layer with the thickness of 50 μm. Then, a backing was applied thereto to obtain Formulation Examples 5 and 6. The details of the prescriptions of Formulation Examples 5 and 6 are shown in Table 1.

Formulation Examples 7 to 10

In these Formulation Examples, pressure-sensitive adhesives other than the above-mentioned acrylic pressure-sensitive adhesive and silicone pressure-sensitive adhesive were used as an additive. Specifically, in Formulation Examples 7 and 6, silodosin was dissolved in a suitable amount of methanol, and in Formulation Examples 9 and 10, silodosin was dissolved in a suitable amount of toluene to prepare silodosin-containing solutions. On the other hand, each of rubber resins shown in Table 1 was dissolved in a suitable amount of toluene as an oily base, a tackifier and a softening agent were then added thereto, and the resulting mixture was stirred and mixed to obtain a homogenous pressure-sensitive adhesive base solution. This pressure-sensitive adhesive base solution was added to the above-mentioned silodosin-containing solution, and the resulting mixture was stirred and mixed to obtain a homogenous silodosin-containing pressure-sensitive adhesive solution. This solution was spread on a release liner that is composed of PET, and then the solvent was dried and removed to form a pressure-sensitive adhesive layer with the thickness of 50 µm. Next, a backing that is a PET film was applied thereto to obtain Formulation Examples 7 to 10. The details of the prescriptions of Formulation Examples 7 to 10 are shown in Table 1.

As for Formulation Examples 1 to 10 obtained in this manner, the presence or absence of crystals of silodosin in the pressure-sensitive adhesive layers when 24 hours elapsed after the production was confirmed with a microscope. The formulation example in which no crystals of silodosin were confirmed was evaluated as good solubility (A), and the formulation examples in which crystals of silodosin were deposited were evaluated as poor solubility (C). These results are shown in Table 1.

was deposited even after a lapse of 24 hours, and it can be seen that the good dissolved state was kept.

On the other hand, Formulation Examples 2 to 10 are comparative examples not using the above-mentioned pressure-sensitive adhesive defined in the present invention and have the contents of silodosin of 5 to 15%. Despite these contents were one half or less of the content in the above Formulation Example 1, crystals were deposited after a lapse of 24 hours.

Specifically, Formulation Examples 2 and 3 are examples using a hydroxyl group-containing acrylic pressure-sensitive adhesive, Formulation Example 4 is an example using an acrylic pressure-sensitive adhesive containing no functional group, and crystals were deposited in all of these examples. Therefore, in the present invention, it can be understood that merely using an acrylic pressure-sensitive adhesive is still insufficient, and it is important to use an acrylic pressure-sensitive adhesive containing a carboxyl group.

Furthermore, Formulation Examples 5 and 6 are examples using a silicone pressure-sensitive adhesive, Formulation Examples 7 to 10 are examples using a rubber resin to which a tackifier and a softening agent are added, and crystals were deposited in all of these examples.

TABLE 1

| Formulation Example No. | Pressure-sensitive adhesive (mass %) | | | | | | Addition ingredient (mass %) | | Addition ingredient (mass %) | | | | Crystalline state after a lapse of 24 hours | |
|---|---|---|---|---|---|---|---|---|---|---|---|---|---|---|
| | Acrylic pressure-sensitive adhesive | | | | Silicone type pressure-sensitive adhesive | | Tackifier | | Softening agent | Rubber resin | | | | |
| | α1-blocker (mass %) Silodosin | Duro-Tak 87-2194 (COOH group) | Duro-Tak 87-2516 (OH group) | Duro-Tak 87-2287 (OH group) | Duro-Tak 87-4098 (no functional group) | Bio-PSA 7-4302 | Bio-PSA 7-4602 | Hydrogenated rosin glycerin ester | Arkon P-100 | Liquid paraffin | Styrene-isoprene-styrene-block copolymer (SIS) | Polyisobutylene (Oppanol B-100) | Polyisobutylene (Oppanol B-50) | Presence or absence of crystals | Evaluation |
| 1 | 30 | 70 | — | — | — | — | — | — | — | — | — | — | — | dissolution | A |
| 2 | 15 | — | 85 | — | — | — | — | — | — | — | — | — | — | deposition | C |
| 3 | 10 | — | — | 90 | — | — | — | — | — | — | — | — | — | deposition | C |
| 4 | 10 | — | — | — | 90 | — | — | — | — | — | — | — | — | deposition | C |
| 5 | 5 | — | — | — | — | 95 | — | — | — | — | — | — | — | deposition | C |
| 6 | 5 | — | — | — | — | — | 95 | — | — | — | — | — | — | deposition | C |
| 7 | 10 | — | — | — | — | — | — | 39.4 | — | 28.1 | 22.5 | — | — | deposition | C |
| 8 | 5 | — | — | — | — | — | — | — | 41.6 | 29.7 | 23.7 | — | — | deposition | C |
| 9 | 5 | — | — | — | — | — | — | 52.8 | — | 21.1 | — | 21.1 | — | deposition | C |
| 10 | 5 | — | — | — | — | — | — | 52.8 | — | 21.1 | — | — | 21.1 | deposition | C |

The following discussion is possible from Table 1.

Formulation Example 1 is an example using the "pressure-sensitive adhesive of a carboxyl group-containing acrylic acid-vinyl copolymer" defined in the present invention. Even though Formulation Example 1 contained silodosin in a high concentration of 30%, no crystal of silodosin (1-2) In Vitro Hairless Rat Skin Permeability Test of Silodosin (Test Example 1)

Next, in order to explore the usefulness of the preparation of the present invention, preparations of the following Examples 1 to 5 and Comparative Examples 1 to 13 were produced as test preparations, and in vitro hairless rat skin permeability tests were conducted. The content of each component in the following examples is shown in Table 2. Note that "—" means 0% in Table 2.

Examples 1 to 5

Silodosin was dissolved in a suitable amount of methanol to prepare a silodosin-containing solution. To the silodosin-containing solution thus obtained were added a carboxyl group-containing acrylic pressure-sensitive adhesive (Duro-Tak 87-2194) and a transdermal absorption promoting agent shown in Table 2 (all are example of the present invention), and the resulting mixture was stirred and mixed to obtain a homogenous silodosin-containing pressure-sensitive adhesive solution. Next, the silodosin-containing pressure-sensitive adhesive solution was spread on a release liner that is composed of PET, and the solvent was dried and removed to form a pressure-sensitive adhesive layer with a thickness of 140 μm. Next, a backing that is a PET film is applied thereto to obtain Examples 1 to 5.

Comparative Examples 1 to 13

Based on the prescription shown in Table 2, preparations of Comparative Examples 1 to 13 were obtained by the same production method as in Examples 1 to 5.

In order to examine the temporal drug permeation amount into a skin of silodosin in each of the above-mentioned preparation examples obtained in this manner, in vitro skin permeability test in a hairless rat was conducted as described below.

First, an excised abdominal skin of male hairless rat (HWY series, 7 weeks old) was put in a Franz diffusion cell, and the above-mentioned each test preparation cut in a round shape (diameter: 14 mm) was applied thereto. In conducting the test, the receptor side was filled with phosphate buffered saline, and hot water of 37° C. was circulated in the water jacket. The receptor solution was sampled with time, the amount of silodosin that permeated the skin was measured by a liquid chromatography, and cumulative drug permeation amounts after 24 hours and 48 hours from the start of the test were calculated. The conditions of the liquid chromatography are as follows:

[HPLC Measurement Conditions]
Column: ODS (Octa Decyl Silyl) column (particle size: 5 μm, inner diameter×length: 4.6×250 mm)
Flow rate: 1.0 mL/min
Column temperature: 25° C.
Wavelength: 269 nm
Mobile phase: phosphate buffer solution (P 2.0)/methanol/acetonitrile=35/60/5 (v/v/v)
The results are shown in Table 2.

TABLE 2

| | | α 1-blocker (mass %) Silodosin | Duro-Tak 87-2194 (COOH group) | Duro-Tak 87-2287 (OH group) | Duro-Tak 87-40913 (no functional group) | Acrylic pressure-sensitive adhesives having a hydroxyl group | Oleyl alcohol | Lauryl alcohol | Lauromacrogol | Isopropyl myristate | Trianetin |
|---|---|---|---|---|---|---|---|---|---|---|---|
| Example | 1 | 30.0 | 50.0 | — | — | — | 20 | — | — | — | — |
| | 2 | 24.0 | 56.0 | — | — | — | 20 | — | — | — | — |
| | 3 | 25.5 | 59.5 | — | — | — | — | 15 | — | — | — |
| | 4 | 27.0 | 63.0 | — | — | — | — | — | 10 | — | — |
| | 5 | 25.5 | 59.5 | — | — | — | — | — | 15 | — | — |
| Comparative Example | 1 | 30.0 | 55.0 | — | — | — | — | — | — | 15 | — |
| | 2 | 30.0 | 50.0 | — | — | — | — | — | — | — | 20 |
| | 3 | 24.0 | 56.0 | — | — | — | — | — | — | — | — |
| | 4 | 24.0 | 56.0 | — | — | — | — | — | — | — | — |
| | 5 | 24.0 | 56.0 | — | — | — | — | — | — | — | — |
| | 6 | 27.0 | 63.0 | — | — | — | — | — | — | — | — |
| | 7 | 27.0 | 63.0 | — | — | — | — | — | — | — | — |
| | 8 | 5.0 | — | 85 | — | — | — | — | — | 10 | — |
| | 9 | 5.0 | — | 85 | — | — | 10 | — | — | — | — |
| | 10 | 5.0 | — | — | 85 | — | — | — | — | 10 | — |
| | 11 | 5.0 | — | — | 85 | — | 10 | — | — | — | — |
| | 12 | 5.0 | — | — | — | 74 | — | — | — | — | 18 |
| | 13 | 9.0 | — | — | — | 79 | — | — | — | — | 9 |

| | | Transdermal absorption promoting agent, (mass %) | | | | | | | Cumulative drug permeation amounts (μg/cm²) | |
|---|---|---|---|---|---|---|---|---|---|---|
| No. | | Propylene-glycol | N-Methyl-2-pyrrolidone | Dimethylsulfoxide | Isopropyl palmitate | Oleic acid | Sorbitan monolaurate | Lauric acid diethanol amide | After 24 hours | After 48 hours |
| Example | 1 | — | — | — | — | — | — | — | 403.1 | 794.3 |
| | 2 | — | — | — | — | — | — | — | 322.9 | 752.0 |
| | 3 | — | — | — | — | — | — | — | 521.2 | 922.7 |
| | 4 | — | — | — | — | — | — | — | 511.9 | 1255.6 |
| | 5 | — | — | — | — | — | — | — | 482.5 | 1877.6 |

TABLE 2-continued

| | | C1 | C2 | C3 | C4 | C5 | C6 | C7 | 24h | 48h |
|---|---|---|---|---|---|---|---|---|---|---|
| Comparative Example | 1 | — | — | — | — | — | — | — | 254.0 | 536.2 |
| | 2 | — | — | — | — | — | — | — | 80.2 | 308.0 |
| | 3 | 20 | — | — | — | — | — | — | 109.2 | 307.1 |
| | 4 | — | 20 | — | — | — | — | — | 116.6 | 333.9 |
| | 5 | — | — | 20 | — | — | — | — | 80.0 | 280.6 |
| | 6 | — | — | — | 10 | — | — | — | 224.5 | 507.8 |
| | 7 | — | — | — | — | 10 | — | — | 190.6 | 435.1 |
| | 8 | — | — | — | — | — | — | — | 42.9 | 134.8 |
| | 9 | — | — | — | — | — | — | — | 133.1 | 303.9 |
| | 10 | — | — | — | — | — | — | — | 146.6 | 296.5 |
| | 11 | — | — | — | — | — | — | — | 171.5 | 348.3 |
| | 12 | — | — | — | — | — | 3 | — | 202.6 | 391.7 |
| | 13 | — | — | — | — | — | — | 3 | 369.0 | 571.3 |

The following discussion is possible from Table 2.

Examples 1 to 5 are examples that satisfy the requirements of the present invention, and the cumulative drug permeation amounts of Examples 1 to 5 tended to increase as compared with those of Comparative Examples 8 to 13 not using the pressure-sensitive adhesive defined in the present invention and Comparative Examples 1 to 7 not using the transdermal absorption promoting agent defined in the present invention. In particular, after a lapse of 48 hours, it was confirmed that the cumulative drug permeation amounts of Examples 1 to 5 significantly increased as compared with those of all of the comparative examples.

Furthermore, among Examples 1 to 5 that satisfy the requirements of the present invention, Example 5 in which lauromacrogol was used as a transdermal absorption promoting agent had a low content of silodosin of 25.5 mass %, whereas the cumulative drug permeation amount significantly increased as high as 1877.6 μg/cm$^2$ after a lapse of 48 hours. It can be clearly seen that this value was about twice as high as the cumulative drug permeation amount (922.7 μg/cm$^2$) of Example 3 having the same composition as in the above Example 5 except for using lauryl alcohol as a transdermal absorption promoting agent.

The usefulness of the present invention can be more clearly confirmed by comparing the examples having the same content of silodosin.

For example, both of Example 1 and Comparative Example 2 have the content of silodosin of 30.0% and the content of the pressure-sensitive adhesive defined in the present invention of 50.0%, and are only different in kind of transdermal absorption promoting agent. Triacetin used in Comparative Example 2 is a transdermal absorption promoting agent often used in the examples of the above-mentioned Patent Document 1. When comparing these, it can be seen that Example 1 that satisfies the requirements of the present invention has an extremely high cumulative drug permeation amount at any of 24 hours after and 48 hours after as compared with that of Comparative Example 2. Therefore, it was confirmed that transdermal absorbability with superior sustainability is exerted in the examples of the present invention.

The similar results were also confirmed when comparing Example 2 and Comparative Examples 3 to 5, and Example 4 and Comparative Examples 6 to 7.

(1-3) Sustained Dissolution Test of Silodosin (Test Example 2)

Furthermore, in order to explore that the transdermal absorption preparation of the present invention is capable of dissolving silodosin for a longer period, by using the respective preparations of Examples 1 to 3 and 5, and Comparative Examples 12 and 13 described above, the crystalline states of these preparations immediately after the production and after a lapse of one week after the production were examined in the same manner as in the above (1-2). Here, the preparation in which no crystals of silodosin were confirmed was evaluated as good solubility (A), the preparation in which a few crystals of silodosin were observed was evaluated as slightly inferior solubility (B), and the preparation in which a lot of crystals of silodosin were confirmed was evaluated as bad solubility (C). Example 4 was not subjected to the test because Example 4 has almost the same component composition as that of Example 5. The results are shown in Table 3.

TABLE 3

| | | Crystals deposition | |
|---|---|---|---|
| No. | | Immediately after the production | After a lapse of one week |
| Examples | 1 | A | B |
| | 2 | A | A |
| | 3 | A | A |
| | 5 | A | A |
| Comparative Examples | 12 | A | C |
| | 13 | A | C |

According to the above test results, in Examples 1 to 3 and 5 that satisfy the requirements of the present invention, crystals of silodosin were not observed immediately after the production of the preparations. Furthermore, only a few crystals of silodosin were observed after a lapse of one week in Example 1, and no crystals of silodosin were observed even after a lapse of one week in Examples 2, 3 and 5.

In contrast, as for Comparative Examples 12 and 13, although the solubility of silodosin was good immediately after the production of the preparations, crystals were deposited after one week in both preparations. As shown in the above Table 2, the contents of silodosin in Comparative Examples 12 and 13 that simulate Patent Document 1 are 5.0% and 9.0%, respectively, they are considerably lower than the contents of silodosin (24.0 to 30.0%) of Examples 1 to 3 and 5 that satisfy the requirements of the present invention, and therefore the cumulative drug permeation amounts were not be able to simply compared. However, these solubilities are as described above, and hence it was confirmed that the examples of the present invention can sustainably maintain a superior solubility despite containing silodosin in a higher concentration than the concentration of silodosin in the preparation described in Patent Document 1.

(1-4) Adhesiveness of Silodosin-Containing Transdermal Absorption Preparation (Test Example 3)

In order to examine adhesiveness to a skin of the silodosin-containing transdermal absorption preparation of the present invention, a cohesive force test (i) and a finger tack test (ii) were conducted as described below. When good results can be obtained in both of these tests, it can be thought that the adhesiveness between the adhesive surface and the skin is sustained, and the transdermal absorbability improves.

(i) Cohesive Force Test

As for the preparations of Examples 1 to 5, and Comparative Examples 12 and 13 described above, a finger was pressed against a surface of the pressure-sensitive adhesive layer of the preparation after a lapse of 24 hours after the production, then the finger was pulled out, and it was visually observed what state (smooth or wavy) the pressure-sensitive adhesive layer on the surface of the preparation was in, and whether or not the pressure-sensitive adhesive layer adhered to the skin. The preparation in which the pressure-sensitive adhesive layer after the test was in a smooth state and the pressure-sensitive adhesive layer did not adhere to the skin was evaluated as having good cohesive force (A), the preparation in which the pressure-sensitive adhesive layer after the test was in a wavy or uneven state and the pressure-sensitive adhesive layer slightly remained on the skin was evaluated as having slightly inferior cohesive force (B), and the preparation in which the pressure-sensitive adhesive layer after the test was in a wavy state or in a state that unevenness was clearly confirmed and the pressure-sensitive adhesive layer adhered to the skin was evaluated as having poor cohesive force (C). The results are shown in Table 4.

(ii) Finger Tack Test

As for the preparations of Examples 1 to 5, and Comparative Examples 12 and 13 described above, a finger tack test was conducted on the pressure-sensitive adhesive layer of the preparation after a lapse of 24 hours after the production. Specifically, a finger was pressed against a surface of the pressure-sensitive adhesive layer, and tackiness (adhesive strength) when the finger was pulled out was evaluated. The preparation having a high adhesive strength was evaluated as being good (A), the preparation having a medium adhesive strength was evaluated as being slightly inferior (B), and the preparation having a low adhesive strength was evaluated as being poor (C). These results are shown in Table 4.

In the present Examples, as for each of the above-mentioned cohesive force test (i) and finger tack test (ii), in the evaluation of the cohesive force test (i), the preparation including no C was determined to be "acceptable" and the preparation including even one C was determined, to be "unacceptable". In the evaluation of the finger tack test (ii), the preparation including an A was determined to be "acceptable" and the preparation including no A was determined to be "unacceptable". As a comprehensive determination of the adhesiveness, the preparations being acceptable in both of the cohesive force test (i) and the finger tack test (ii) were determined as having an excellent adhesiveness to the skin (acceptable).

TABLE 4

| No. | | Adhesiveness | |
|---|---|---|---|
| | | Cohesive force | Finger tack |
| Examples | 1 | B | A |
| | 2 | A | A |
| | 3 | A | A |
| | 4 | A | A |
| | 5 | A | A |

TABLE 4-continued

| No. | | Adhesiveness | |
|---|---|---|---|
| | | Cohesive force | Finger tack |
| Comparative Examples | 12 | C | C |
| | 13 | B | B |

It can be seen from the above Table 4 that Examples 1 to 5 that satisfy the requirements of the present invention show excellent characteristics even when being subjected to any of the tests and have an excellent adhesiveness to the skin. In contrast, Comparative Example 12 that does not satisfy the requirements of the present invention was determined to be unacceptable (C) in all of the above-mentioned tests. Although the test results of Comparative Example 13 were slightly improved as compared with those of Comparative Example 12, the comprehensive determination remained unacceptable.

(2) Experiments Using Tamsulosin as an Active Ingredient

Here, the following experiments were performed using tamsulosin (free form) as an active ingredient.

(2-1) Solubility Test of Tamsulosin (Basic Experiment)

First, in order to explore the usefulness of the pressure-sensitive adhesive used in the present invention, the following formulation examples 11 to 13 composed of tamsulosin and various pressure-sensitive adhesives and containing no transdermal absorption promoting agent were produced to examine the solubility of tamsulosin. The content of each component in each of the formulation examples is shown in Table 5. In Table 5, "—" means 0%.

Formulation Example 11

Tamsulosin was dissolved in a suitable amount of ethyl acetate to prepare a tamsulosin-containing solution. To the tamsulosin-containing solution thus obtained was added a carboxyl group-containing acrylic pressure-sensitive adhesive (Duro-Tak 87-2194), the resulting mixture was stirred and mixed to obtain a homogenous tamsulosin-containing pressure-sensitive adhesive solution. Next, this tamsulosin-containing pressure-sensitive adhesive solution was spread on a release liner that is composed of PET, and then the solvent was dried and removed to form a pressure-sensitive adhesive layer with the thickness of 150 µm. Then, a backing that is a PET film was applied thereto to obtain Formulation Example 11. The details of the prescription of Formulation Example 11 are shown in Table 5.

Formulation Examples 12 and 13

Based on the prescription shown in Table 5, preparations of Formulation Examples 12 and 13 were obtained by the same production method as in Formulation Example 11 except for using a different acrylic pressure-sensitive adhesive.

As for Formulation Examples 11 to 13 obtained in this manner, the presence or absence of crystals of tamsulosin in the pressure-sensitive adhesive layers when 24 hours elapsed after the production was measured and evaluated in the same manner as in the above-mentioned (1-1). These results are shown in Table 5.

TABLE 5

| Formulation Example No. | α 1-blocker (mass %) Tamsulosin | Acrylic pressure-sensitive adhesive (mass %) | | | Crystalline state after a lapse of 24 hours | |
|---|---|---|---|---|---|---|
| | | Duro-Tak 87-2194 (COOH group) | Duro-Tak 87-2516 (OH group) | Duro-Tak 87-4098 (no functional group) | Presence or absence of crystals | Evaluation |
| 11 | 5 | 95 | — | — | dissolution | A |
| 12 | 2 | — | 98 | — | deposition | C |
| 13 | 1 | — | — | 99 | deposition | C |

The following discussion is possible from Table 5.

Formulation Example 11 is an example using the "pressure-sensitive adhesive of a carboxyl group-containing acrylic acid-vinyl copolymer" defined in the present invention. Even though Formulation Example 11 contained tamsulosin in a high concentration of 5%, no crystal of tamsulosin was deposited even after a lapse of 24 hours, and it was found that the good dissolved state was kept.

On the other hand, Formulation Examples 12 and 13 are comparative examples not using the above-mentioned pressure-sensitive adhesive defined in the present invention and have the contents of tamsulosin of 1 to 2%. Despite these contents were less than one half of the content in the above Formulation Example 11, crystals were deposited after a lapse of 24 hours.

Specifically, Formulation Example 12 is an example using a hydroxyl group-containing acrylic pressure-sensitive adhesive, Formulation Example 13 is an example using an acrylic pressure-sensitive adhesive containing no functional group, and crystals were deposited in both. Therefore, it can be understood that in the present invention, merely using an acrylic pressure-sensitive adhesive is still insufficient, and it is important to use an acrylic pressure-sensitive adhesive containing a carboxyl group.

(2-2) In Vitro Hairless Rat Skin Permeability Test of Tamsulosin (Test Example 1)

Next, in order to explore the usefulness of the preparation of the present invention, preparations of the following Examples 6 to 8 and Comparative Examples 14 to 18 were produced as test preparations, and in vitro hairless rat skin permeability tests were conducted. The content of each component in the following examples is shown in Table 6. Note that "—" means 0% in Table 6.

Examples 6 to 8

Tamsulosin was dissolved in a suitable amount of ethyl acetate to prepare a tamsulosin-containing solution. To the tamsulosin-containing solution thus obtained were added a carboxyl group-containing acrylic pressure-sensitive adhesive (Duro-Tak 87-2194) and a transdermal absorption promoting agent shown in Table 6 (all are examples of the present invention), and the resulting mixture was stirred and mixed to obtain a homogenous tamsulosin-containing pressure-sensitive adhesive solution. Next, the tamsulosin-containing pressure-sensitive adhesive solution was spread on a release liner that is composed of PET, and the solvent was dried and removed to form a pressure-sensitive adhesive layer with a thickness of 150 μm. Next, a backing that is a PET film is applied thereto to obtain Examples 6 to 8. The details of the prescription of Examples 6 to 8 are shown in Table 6.

Comparative Examples 14 to 18

Based on the prescription shown in Table 6, preparations of Comparative Example 14 to 18 were obtained by the same production method as in Examples 6 to 8.

In order to examine the cumulative drug permeation amount into a skin after a lapse of 72 hours from the start of the test in each of the above-mentioned preparation examples obtained in this manner, in vitro skin permeability test in a hairless rat was conducted in the same manner as in the above-mentioned (1-2) other than the HPLC measurement conditions.

[HPLC measurement conditions]

Column: ODS column (particle size: 3 μm, inner diameter×length: 3.0×150 mm)

Flow rate: 0.5 mL/min

Column temperature: 40° C.

Wavelength: 225 nm

Mobile phase: sodium perchlorate buffer solution (PH 2.0)/acetonitrile=60/40 (v/v)

The results are shown in Table 6.

TABLE 6

| No. | | α 1-blocker (mass %) Tamsulosin | Acrylic pressure-sensitive adhesive (mass %) Duro-Tak 87-2194 (COOH group) | Transdermal absorption promoting agent (mass %) | | | | | | | | Cumulative drug permeation amounts after 72 hours (μg/cm²) |
|---|---|---|---|---|---|---|---|---|---|---|---|---|
| | | | | Oleyl alcohol | Lauryl alcohol | Lauromacrogol | Isopropyl myristate | Triacetin | Propylene-glycol | Dimethyl-sulfoxide | Oleic acid | |
| Example | 6 | 5 | 75 | 20 | — | — | — | — | — | — | — | 5.3 |
| | 7 | 5 | 80 | — | 15 | — | — | — | — | — | — | 14.2 |
| | 8 | 5 | 80 | — | — | 15 | — | — | — | — | — | 107.6 |

TABLE 6-continued

| No. | | α 1-blocker (mass %) Tamsulosin | Acrylic pressure-sensitive adhesive (mass %) Duro-Tak 87-2194 (COOH group) | Transdermal absorption promoting agent (mass %) | | | | | | | | Cumulative drug permeation amounts after 72 hours ($\mu$g/cm$^2$) |
|---|---|---|---|---|---|---|---|---|---|---|---|---|
| | | | | Oleyl alcohol | Lauryl alcohol | Lauromacrogol | Isopropyl myristate | Triacetin | Propylene-glycol | Dimethyl-sulfoxide | Oleic acid | |
| Comparative Example | 14 | 5 | 75 | — | — | — | — | — | 20 | — | — | 3.0 |
| | 15 | 5 | 75 | — | — | — | — | 20 | — | — | — | 1.4 |
| | 16 | 5 | 75 | — | — | — | — | — | — | 20 | — | 0.7 |
| | 17 | 5 | 75 | — | — | — | 20 | — | — | — | — | 4.3 |
| | 18 | 5 | 85 | — | — | — | — | — | — | — | 10 | 0.3 |

The following discussion is possible from Table 6.

The cumulative drug permeation amounts of Examples 6 to 8 that satisfy the requirements of the present invention increased as compared with those of Comparative Examples 14 to 18 not using the transdermal absorption promoting agent defined in the present invention. In particular, in Example 8 in which lauromacrogol was used as a transdermal absorption promoting agent, the cumulative drug permeation amount after a lapse of 72 hours significantly increased. Therefore, it is thought that even in the case where tamsulosin is contained as an active ingredient, more excellent transdermal absorption action can be obtained by using lauromacrogol as a transdermal absorption promoting agent as in the case containing silodosin.

The usefulness of the present invention can be more clearly confirmed by comparing Example 6 and Comparative Examples 14 to 17 having the same contents of tamsulosin and the pressure-sensitive adhesive.

That is, all of those examples have the content of tamsulosin of 5% and the content of the pressure-sensitive adhesive defined in the present invention of 75%, and are only different in kind of transdermal absorption promoting agent. Triacetin used in Comparative Example 15 and isopropyl myristate used in Comparative Example 17 are transdermal absorption promoting agents described in the above-mentioned Patent Document 1. When comparing these, it can be found that Example 6 that satisfies the requirements of the present invention has an extremely high cumulative drug permeation amount after a lapse of 72 hours as compared with those of Comparative Examples 14 to 17. Therefore, it was confirmed that transdermal absorbability with superior sustainability is exerted for a long period of 72 hours in the examples of the present invention.

The invention claimed is:

1. A transdermal absorption preparation comprising:
   silodosin or a salt thereof, or tamsulosin or a salt thereof as an active ingredient,
   an acrylic pressure-sensitive adhesive that comprises a copolymer of at least one (meth)acrylic acid monomer and at least one vinyl monomer and that contains a carboxyl group, and
   at least one transdermal absorption promoting agent selected from the group consisting of oleyl alcohol, lauryl alcohol, and lauromacrogol,
   wherein the vinyl monomer comprises at least one selected from the group consisting of vinyl acetate, N-vinyl-2-pyrrolidone, acrylamide, dimethylacrylamide, diethylacrylamide, methacrylamide, N-methylolacrylamide, glycidyl acrylate, and glycidyl methacrylate, and
   wherein the transdermal absorption preparation does not include fatty acid ester and/or fatty acid amide.

2. The transdermal absorption preparation according to claim 1, wherein a content of the silodosin or a salt thereof in the transdermal absorption preparation is 10 to 50 mass % in terms of a free form of silodosin.

3. The transdermal absorption preparation according to claim 1, wherein a content of the tamsulosin or a salt thereof in the transdermal absorption preparation is 0.5 to 10 mass % in terms of a free form of tamsulosin.

4. The transdermal absorption preparation according to claim 1, wherein the transdermal absorption promoting agent is lauromacrogol.

5. The transdermal absorption preparation according to claim 2, wherein the transdermal absorption promoting agent is lauromacrogol.

6. The transdermal absorption preparation according to claim 3, wherein the transdermal absorption promoting agent is lauromacrogol.

7. A transdermal absorption preparation consisting of:
   silodosin or a salt thereof, or tamsulosin or a salt thereof as an active ingredient,
   an acrylic pressure-sensitive adhesive that comprises a copolymer of at least one (meth)acrylic acid monomer and at least one vinyl monomer and that contains a carboxyl group,
   at least one transdermal absorption promoting agent selected from the group consisting of oleyl alcohol, lauryl alcohol, and lauromacrogol,
   a softening agent,
   a water-soluble polymer,
   an inorganic filler,
   an antioxidant, and
   optionally a preservative, an algefacient, a fungicide, a flavoring agent, and a colorant,
   wherein the vinyl monomer comprises at least one selected from the group consisting of vinyl acetate, N-vinyl-2-pyrrolidone, acrylamide, dimethylacrylamide, diethylacrylamide, methacrylamide, N-methylolacrylamide, glycidyl acrylate, and glycidyl methacrylate, and
   wherein the transdermal absorption preparation does not include fatty acid ester and/or fatty acid amide.

* * * * *